(12) United States Patent
Tabacco et al.

(10) Patent No.: US 6,498,041 B1
(45) Date of Patent: Dec. 24, 2002

(54) OPTICAL SENSORS FOR RAPID, SENSITIVE DETECTION AND QUANTITATION OF BACTERIAL SPORES

(75) Inventors: Mary Beth Tabacco, Belmont, MA (US); Laura C. Taylor, Waterford, NY (US)

(73) Assignee: Echo Technologies, Inc., Alexandria, VA (US)

( * ) Notice: Subject to any disclaimer, the term of this patent is extended or adjusted under 35 U.S.C. 154(b) by 162 days.

(21) Appl. No.: 09/641,240

(22) Filed: Aug. 18, 2000

(51) Int. Cl.[7] ............................ G01N 21/76; C12Q 1/04
(52) U.S. Cl. ......................... 436/172; 436/79; 435/34; 435/39; 435/287.1; 435/287.9; 435/288.7; 250/252.1; 250/361 R; 250/361 C; 250/362; 250/368
(58) Field of Search ..................... 436/79, 172; 435/34, 435/39, 287.1, 287.9, 288.7; 250/252.1, 361 R, 361 C, 362, 368

(56) References Cited

U.S. PATENT DOCUMENTS 5,876,960 A * 3/1999 Rosen

OTHER PUBLICATIONS

Belgrader, P., et al., "A Minisonicator to Rapidly Disrupt Bacterial Spores for DNA Analysis," *Anal. Chem* 71:4232–4236 (1998).

Beverly, M.B., et al., "A Rapid Approach for the Detection of Dipiconnic Acid in Bacterial Spores Using Pyrolysis/Mass Spectrometry," *Rapid Comm. in Mass Spec.* 10(4):455–458 (1996).

Tuminello, P.S., et al., *Applied Optics* 36(13):2818–2824 (1997).

Nudelman, R., et al., "Fluorescence of Dipicolinic Acid as a Possible Component of the Observed UV Emission Spectra of Bacterial Spores," in Leonelli, J., et al., Air Monitoring and Detection of Chemical and Biological Agents, SPIE Proceedings Seris vol. 3533: 190–195 (1998).

Rosen, D.L., et al., "Bacterial Spore Detection and Determination by Use of Terbium Dipicolinate Photoluminescence," *Analytical Chemistry* 69(6):1082–1085 (1997).

Pellegrino, P.M., et al., "Bacterial Endospore Detection Using Terbium Dipicolinate Photoluminescence in the Presence of Chemical and Biological Materials," *Anal. Chem.* 70:1755–1760 (1996).

School, P.F., et al., "The Development of Matrix–Assisted Laser Desorption/Ionization Time–of–Flight Mass Spectrometry for the Detection of Biological Warfare Agent Aerosols," *Johns Hopkins APL Technical Digest* 20(3):343–351 (1999).

Quinlan, J.J., et al., "Monoclonal Antibody–Based ELISAS for the Detection of Bacterial Spores," *Journal of Rapid Methods and Automation in Microbiology* 6:1–16 (1998).

(List continued on next page.)

Primary Examiner—Jill Warden
Assistant Examiner—Monique T. Cole
(74) Attorney, Agent, or Firm—Browdy and Neimark, P.L.L.C.

(57) ABSTRACT

Bacterial spores can be rapidly and sensitively detected and quantified based upon molecular recognition of unique chemicals in the spore coat. Spores can be detected and assayed based upon the calcium concentration in bacterial spore coats using the calcium which is unique to the bacterial spores. Since spores contain a high concentration of calcium relative to other biological materials, fluorescent calcium-sensitive indicators are used to detect $Ca^{+2}$ displaced from the spore case or free in solution or from the aerosol phase. Visibly excitable fluorescent dyes provide a sensitive and selective means to monitor changes in spore concentration and avoid difficulties associated with laser or UV-excitation.

9 Claims, 11 Drawing Sheets

OTHER PUBLICATIONS

Quinlan, J.J., et al., "Monoclonal Antibodies for Use in Detection of Bacillus and Clostridium Sports," *Applied and Environmental Microbiology* 63(2):482–487 (1997).

Blake, M., et al., "Immunomagnetic Dectection of *Bacillus stearothermphilus* Spores in Food and Environmental Samples," *Applied and Environmental Microbiology* 63(5): 1643–1646 (1997).

Rodriguez–Romo, L.A., et al., "Detection of Enterotoxigenic *Clostridium perfringens* in Spices Used in Mexico by Dot Blotting Using a DNA probe," *Journal of Food Protection* 61(2):201–204 (1998).

Belgrader, P., et al., "Autonomous System for Pathogen Detection and Identification," in SPIE vol. 3533: 198–206 (1998).

Sperveslage, J., et al., "Detection of Bacterial Contamination, including *Bacillus* spores, in Dry Growth Media and in Milk by Identification of Their 16S rDNA by Polymerase Chain Reaction," *Journal of Microbiological Methods* 26:219–224 (1996).

Herman, L.M.F., et al., "Identification and Detection of *Bacillus sporothermodurans* Spores in 1, 10, and 100 Milliliters of Raw Milk by PCR," *Applied and Environmental Microbiology* 63(6):3139–3143 (1997).

Bruno, J.G., et al., "In vitro Selection of DNA Aptamers to Anthrax Spores with Electrochemiluminescence Detection," *Biosensors and Bioelectronics* 14:457–464 (1999).

Snyder, A.P., et al., "Detection of the Picolinic Acid Biomarker in Bacillus Spores Using a Potentially Field–POrtable Pyrolysis–Gas Chromatography–Ion Mobility Spectrometry System," *Field Analytical Chemistry and Technology*, 1(1):49–58 (1996).

* cited by examiner

OPTICAL SENSORS FOR RAPID, SENSITIVE DETECTION AND QUANTITATION OF BACTERIAL SPORES

FIELD OF THE INVENTION

The present invention relates to optical sensors for detecting and quantitating bacterial spores.

BACKGROUND OF THE INVENTION

The threat from biological weapons as tools of modern warfare and urban terrorism is increasing. Development of early detection, counter measures, and remediation technology is a high priority in many military, government and private laboratories around the world. Biological warfare (BW) agents of critical concern are bacterial spores, such as *Bacillus anthracis* (anthrax), *Clostridium tetani* (tetanus), and *Clostridium botulinum* (botulism). Spores, produced by certain types of gram positive bacteria in response to starvation, are non-growing, heat-resistant, dehydrated, and resistant to extremes of temperature, pH, desiccation, radiation, and chemical agents.[1,2] Due to their high stability, spores are difficult to stain using typical cell biology methods and, consequently, are challenging to detect and enumerate. This stability and difficulty with conventional detection methods, in turn, make them an attractive tool for use in BW weapons.

An effective bacterial spore detection method must be rapid, sensitive, selective, and cost-effective. In addition to these criteria, the technology must be easily incorporated into a handheld or field-portable device that has low power requirements, requires little maintenance, and may be operated by untrained personnel. In recent years several detection techniques have been explored including transmittance and reflectance,[3] Pyrolysis/Mass Spectrometry,[4] Pyrolysis-Gas Chromatography-Ion Mobility Spectrometry (Py-GC/IMS),[5] PCR-amplified DNA sequences,[6]f 7 Enzyme-Linked Immunosorbent Assays (ELISAs),[8,9] Matrix-Assisted Laser Desorption/Ionization Time-Of-Flight Mass Spectrometry (MALDI-OF-MS),[10] and detection of terbium dipicolinate complexes.[11,12] Although many of these technologies have been demonstrated as viable for spore detection, most require substantial operator expertise and incorporation of these methods into a low-cost field-portable device may not be possible. Moreover, spores are resistant to detection by a variety of other methods, including conventional microscopic staining, DNA probes, and antibody detection.

SUMMARY OF THE INVENTION

It is an object of the present invention to overcome the aforesaid deficiencies in the prior art. It is another object of the present invention to provide a method for detecting and quantifying bacterial endospores.

It is another object of the present invention to provide a system for detecting and quantifying bacterial endospores.

It is yet another object of the present invention to detect and quantify bacteria using visibly excitable fluorescent dyes.

According to the present invention, bacterial spores can be rapidly and sensitively detected and quantified based upon molecular recognition of unique chemicals in the spore coat. Spores can be detected and assayed based upon the calcium concentration in bacterial spore coats using the calcium which is unique to the bacterial spores.

Since spores contain a high concentration of calcium relative to other biological materials, fluorescent calcium-sensitive indicators are used to detect $Ca^{+2}$ displaced from the spore case or free in solution or from the aerosol phase. Visibly excitable fluorescent dyes provide a sensitive and selective means to monitor changes in spore concentration and avoid difficulties associated with laser or UV-excitation.

The fluorescent calcium indicator is immobilized in a polymer membrane for solid-state sensing. This technique makes it possible to measure sample fluorescence without further washing or filtering steps, thus increasing the speed of data acquisition and reducing possible sources of error. The cost of assaying is much lower than with conventional methods, and no laboratory manipulation or skilled user is required. The technology is applicable to real-time detection of bacterial spores, and the chemistry is immune to the presence of bacteria, viruses, pollen, and fungal spores. Because the process of this invention detects bacterial spores, this process can be used to discriminate potentially pathogenic spore-forming bacteria from non spore-forming genera.

According to the present invention, a visibly excitable fluorescent calcium-sensitive indicator is used with optical fibers and disposable planar glass coupons to provide a simple biosensor. The use of visibly excitable fluorescent dyes provides a sensitive and selective means to monitor changes in spore concentration, and avoids the high cost, power consumption, and complexity associated with laser or UV-excitation. The calcium in the spores is mostly complexed with dipicolinic acid also unique to the spore and not found in the corresponding vegetative cells.

DETAILED DESCRIPTION OF THE INVENTION

The spore detection scheme of the present invention uses a sensor created by combining a fluorescent calcium-sensitive indicator, such as calcein in a viscous membrane on planar coupons. The coupons are preferably made of silica glass. The sensor coupon is affixed to the distal end of an optical fiber, which provides excitation light and collects the fluorescence emission. Aqueous micro-droplets of bacterial spores are added to the sensor, and the resulting increase in fluorescence intensity is monitored This assay is based on the high concentration of calcium dipicolinic acid complex unique to bacterial spores, and the use of fluorescence spectroscopy to detect and quantify spore concentration. This sensor technology is applicable to near real-time detection of bacterial spores without interference from light scattering or other ambient biological materials such as bacteria, pollen, viruses, and fungal spores.

While micro droplets are not essential, a totally dry environment will not support the reaction. Aerosolized spores that deposit onto a film, e.g., glycerol/calcein, can be detected by this method.

A number of different molecular probes can be used to detect the calcium in bacterial spores according to the present invention, including fluorescent calcium indicators excited with ultraviolet light, fluorescent calcium indicators excited with visible light, and fluorescent calcium indicator conjugates. Nonlimiting examples of some of these indicators are shown below:

containing the DNA probe was virtually zero compared to the chemistry containing a calcium-sensitive indicator. The data, shown in FIG. 6, demonstrate the inability to stain spores using DNA probes.

Reactivity of Bacteria to Calcium Indicators versus DNA Probes

The reactivity of the bacteria was characterized by exposing the bacteria to chemistries containing calcium indicators or DNA probes. The data were analyzed by averaging the integrated signal from three replicates and calculating the standard deviation. A control measurement was subtracted from all data points to eliminate background fluorescence. The fluorescence intensity resulting from the chemistry containing the calcium-sensitive indicator was negligible compared to the chemistry containing a DNA probe. The data, shown in FIG. 7, demonstrate the specificity of the calcium indicators for spores.

TABLE 1

| Molecular Probes | | | | | |
|---|---|---|---|---|---|
| Fluorescent Ca (2+) Excited with UV Light | | Fluorescent Ca (2+) Indicators Excited with Visible Light | | Fluorescent Ca (2+) Indicator Conjugates | |
| Cat # | Product Name | Cat # | Product Name | Cat # | Product Name |
| B-14170 | benzothiaza-1 | C-3010 | Calcium Green-1 | C-6804 | Calcium Green-C18 |
| B-14172 | benzothiaza-2 | C-3730 | Calcium Green-2 | C-6765 | Calcium Green-1 dextran |
| B-6810 | bis-fura-2 | C-3737 | Calcium Green-5N | F-6792 | fura-C18 |
| B-6790 | BTC | C-3013 | Calcium Orange | F-3029 | fura dextran |
| F-1200 | fura-2 | C-6770 | Calcium Orange-5N | I-3032 | indo dextran |
| F-14180 | fura-FF | F-1240 | fluo-3 | O-6798 | Oregon Green ® 488 BAPTA-1 dextran |
| F-14174 | fura-4F | F-14200 | fluo-4 | | |
| F-14176 | fura-5F | F-14203 | fluo-5N | | |
| F-14178 | fura-6F | F-14221 | fluo-5F | | |
| I-1202 | indo-1 | F-14219 | Fura Red | | |
| M-1290 | mag-fura-2 | M-14205 | mag-fluo-4 | | |
| M-3103 | mag-fura-5 | M-3733 | Magnesium Green | | |
| M-1293 | mag-indo-1 | M-14213 | mag-rhod-2 | | |
| Q-1287 | quin-2 | M-14215 | mag-X-rhod-1 | | |
| | | O-6806 | Oregon Green ® 488 BAPTA-1 | | |
| | | O-6808 | Oregon Green ® 488 BAPTA-2 | | |
| | | O-6812 | Oregon Green ® 488 BAPTA-5N | | |
| | | R-14220 | rhod-2 | | |
| | | R-14224 | rhod-5F | | |
| | | X-14209 | X-rhod-1 | | |
| | | X-14211 | X-rhod-5N | | |

Light Scatter Interferences

As shown in FIG. 5, light scattering off the dense spore coat is characterized by comparing the signal from 0.75 mm-diameter polystyrene beads [a mimic of the spore shape and size (1–2 mm in diameter)] and spore suspensions. The data were analyzed by averaging the integrated signal from three replicates and calculating the standard deviation. A control measurement was subtracted from all data points to eliminate background fluorescence. If light scattering off the spore coat is a factor, then the signal should be detectable with the addition of polystyrene beads. In this case, when compared to the fluorescence intensity of spore concentration, the fluorescence signal intensity of the beads was virtually negligible. These results indicate that light scattering off the spore coat is not a factor in this assay.

Reactivity of Spores to Calcium Indicators versus DNA Probes

The reactivity of the spores was characterized by exposing the spores to chemistries containing calcium indicators or DNA probes. The data were analyzed by averaging the integrated signal from three replicates and calculating the standard deviation. A control measurement was subtracted from all data points to eliminate background fluorescence. The fluorescence intensity resulting from the chemistry The sensor configuration is shown in FIGS. 1A and 1B, using an Acton Research Corporation SpectraPro(R) double monochromator 100. Light from a xenon lamp 101 is collimated, passed through an excitation filter 103 and beamsplitter 105, and focused with a 16× microscope objective 106 on the proximate end of an 800 micron diameter optical fiber 107. The incident excitation light is propagated through the fiber to the fluorescent probe and collected back through the fiber, reflected off the beam splitter, focused by a lens 104, passed through an emission filter and detected by a photomultiplier tube 102.

As shown in FIG. 1B, the sample 110 is pipetted onto a planar glass coupon 109 and positioned on the platform 108 so that the micro-droplet of sample completely covers the distal end of the optical fiber.

The initial step in developing an assay for spore detection was to determine the sensitivity, or limit of detection, of the sensing chemistry toward $Ca^{2+}$ ions. A calibration curve of $CaCl_2$ concentration with the least squares fit is shown in FIG. 2. The correlation coefficient, $R^2$, is 0.9937. The limit of detection was calculated by dividing three times the standard deviation of the control (no $CaCl_2$) by the slope of the curve, yielding a value of 35 nM $Ca^{2+}$. Since the calculated concentration of $Ca_{2+}$ in a suspension of 1.8 e7 spores per mL is approximately 45 nM, the sensing chemistry has sufficient sensitivity to detect bacterial spores.

Figure 1A:
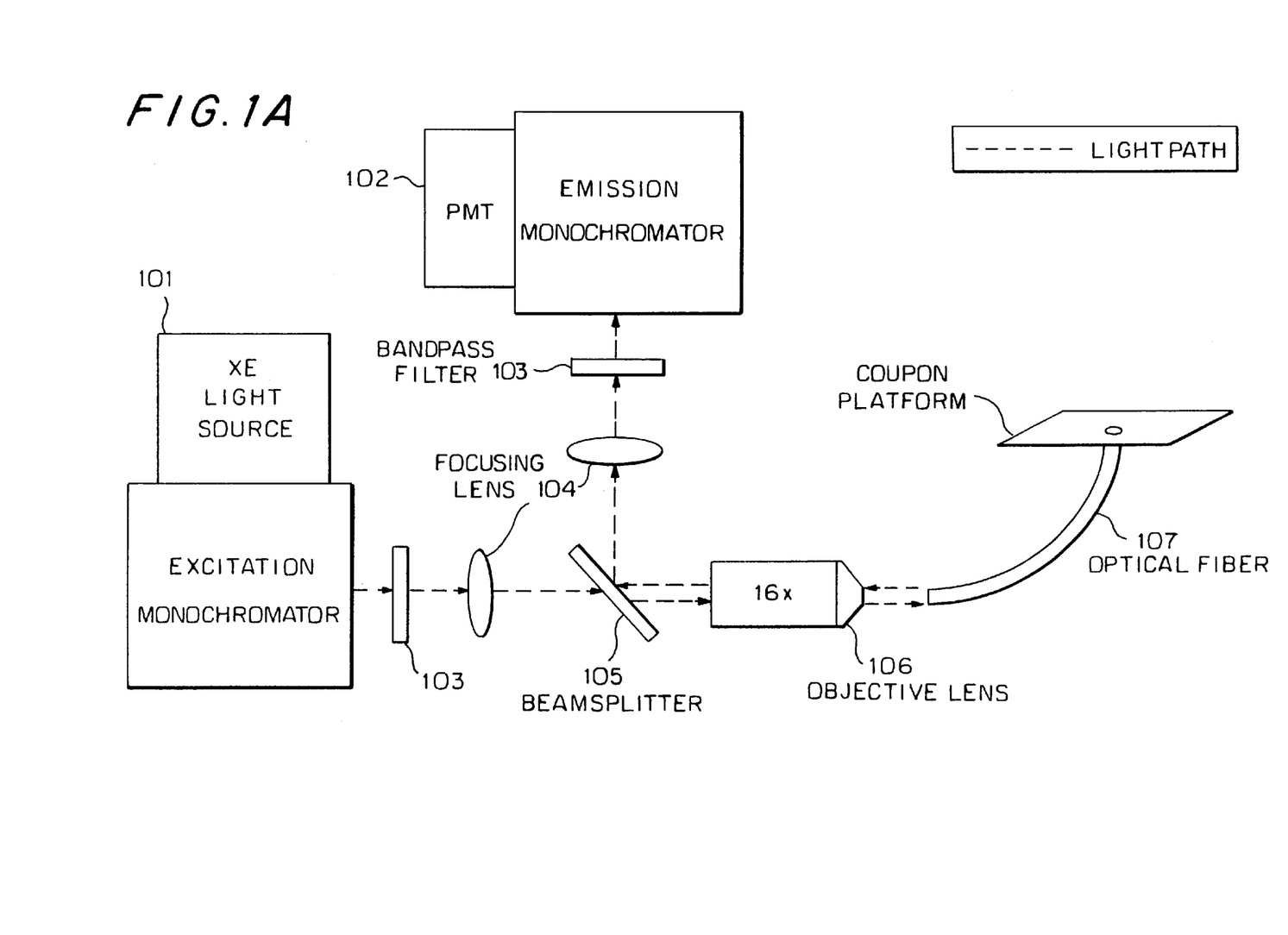
FIG. 1A shows a double monochromator for sensing bacterial spores according to the present invention.
Figure 1B:
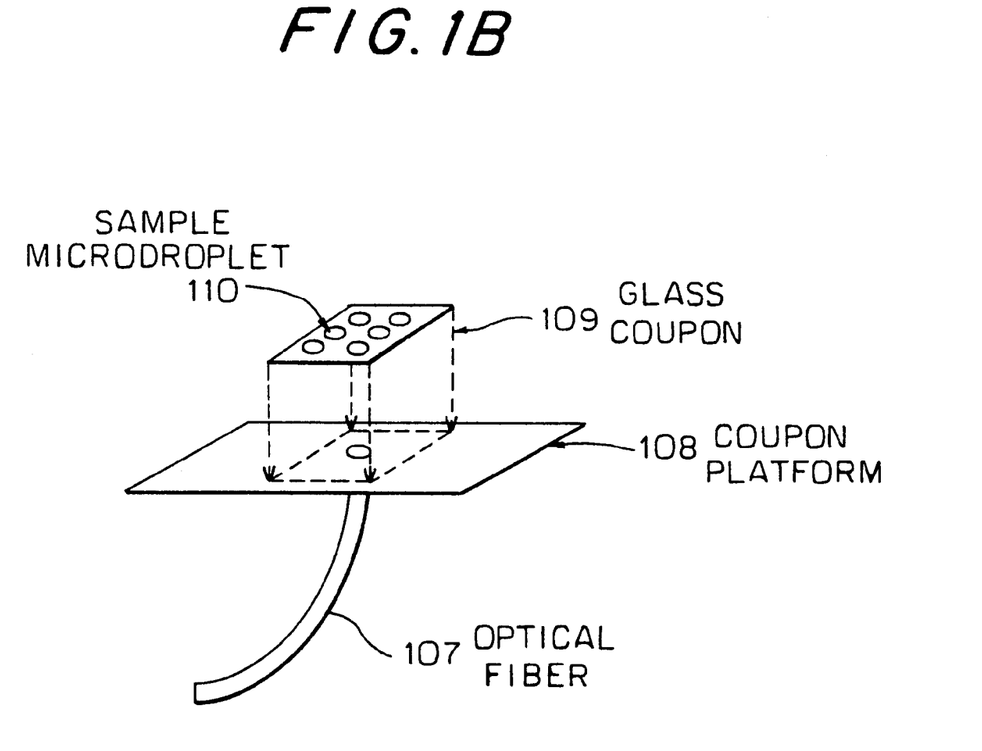
FIG. 1B shows a sample on a planar glass coupon.
Figure 2:
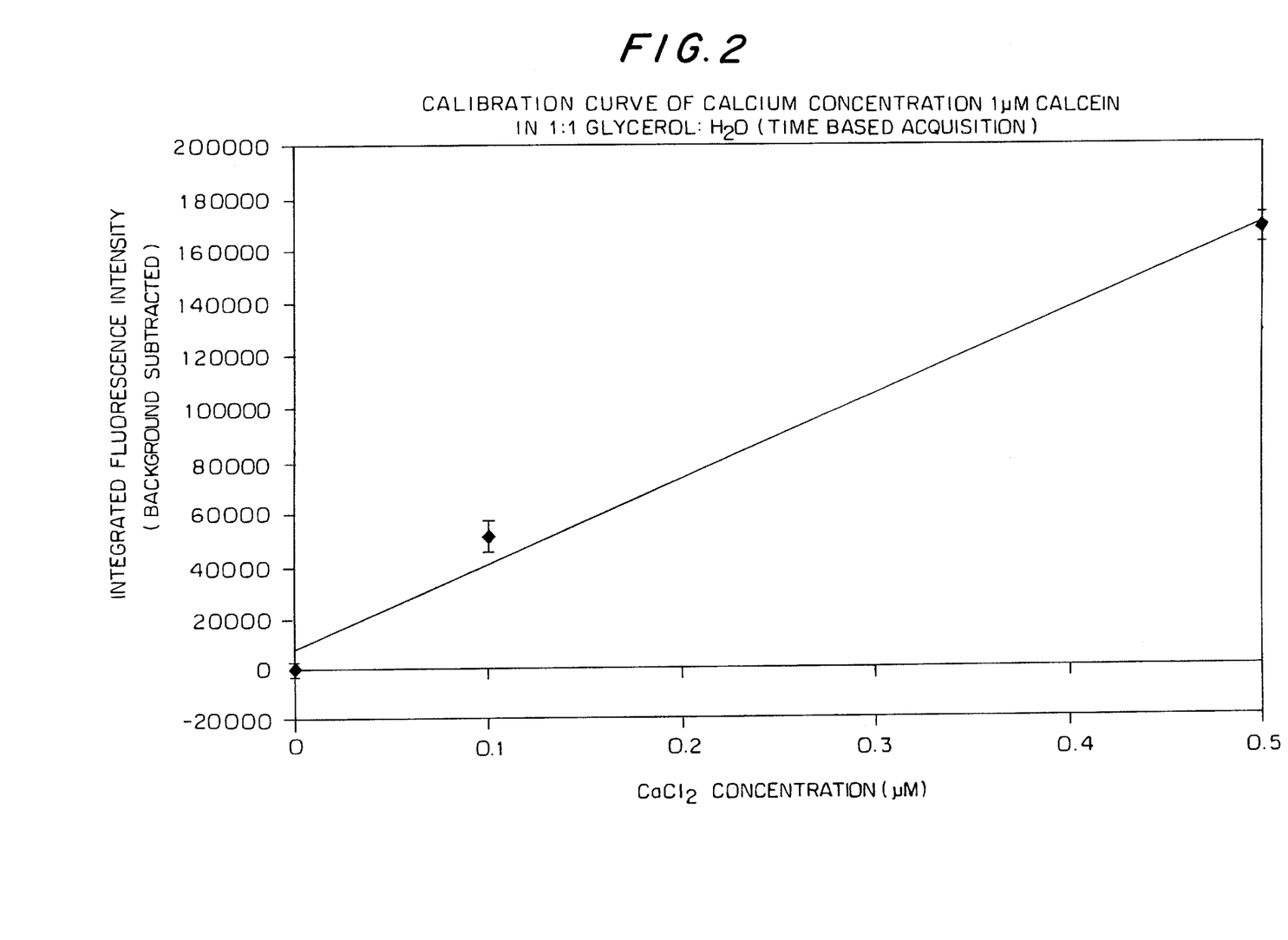
FIG. 2 shows a calibration curve of $Ca^{2+}$ concentration.
Figure 3:
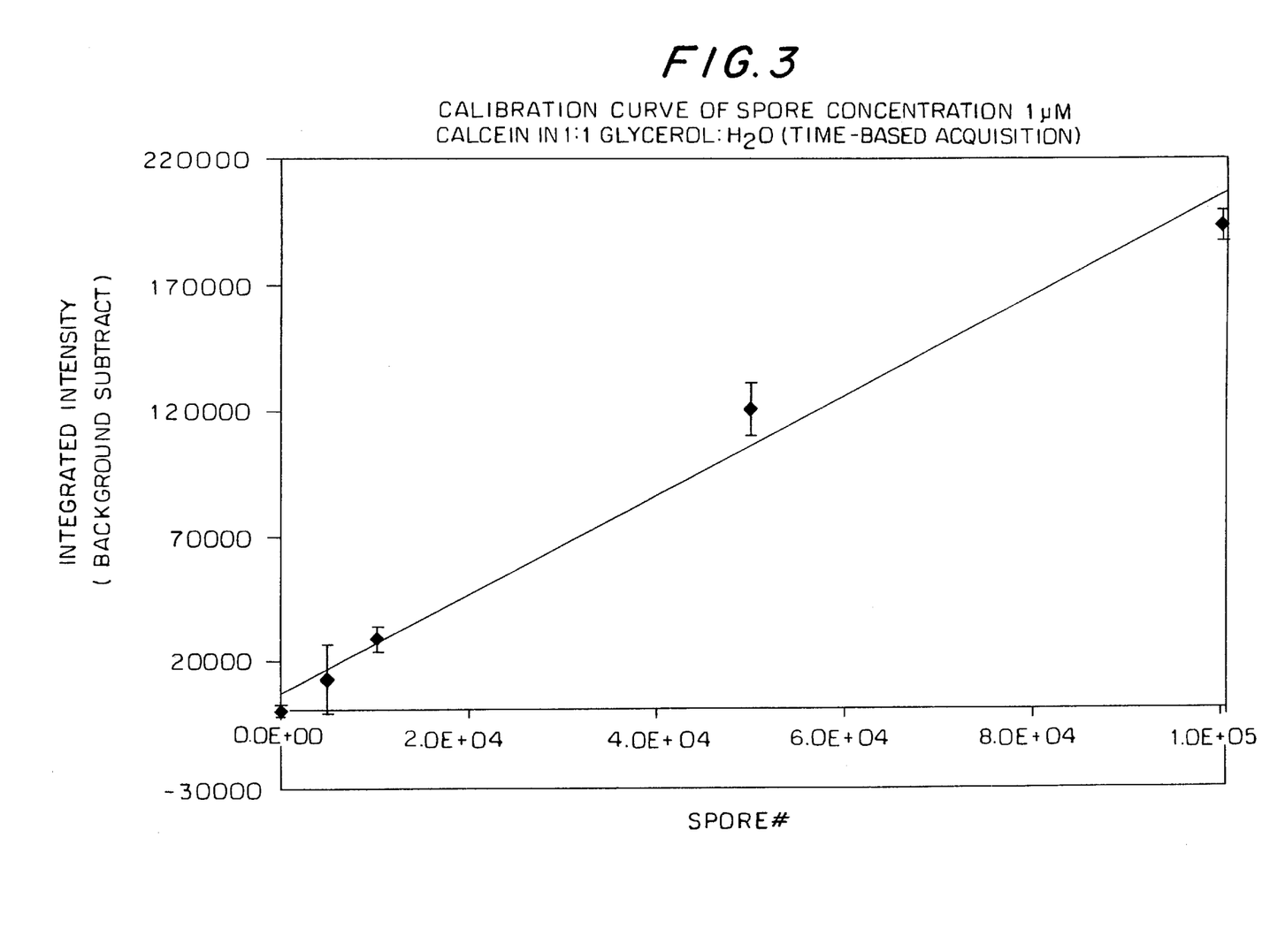
FIG. 3 shows a calibration curve of spore concentration.

The second step in developing the assay was to define the spectral response curves resulting from spore/dye interactions. The spectral changes with varying spore concentration are shown in FIG. 3, showing that the peak fluorescence emission at 515 nm decreases with decreasing spore concentration. Once the spectral characteristics of the assay were determined, further data were taken with a time-based acquisition by setting the excitation and emission wavelengths at their maxima(485 nm and 515 nm, respectively) and integrating over time. Collecting the raw signal data via time-based acquisition rather than collecting the entire spectrum greatly reduces the measurement time and improves the reproducibility of the measurement (i.e., less photo bleaching of the indicator dye).

FIG. 3 shows a calibration curve with the least squares fit of spore concentration that determines the sensitivity or limit of detection (LOD) of the sensing chemistry toward spores. The data were analyzed by averaging the integrated signal from three replicates and calculating the standard deviation. A control measurement (no spores) was subtracted from all data points to eliminate background fluorescence. The correlation coefficient, $R^2$, is 0.9928. The LOD was calculated by dividing 3 times the standard deviation of the control (no spores) by the slope of the curve. The calculated LOD of this assay is 1763 spores.

Figure 4:
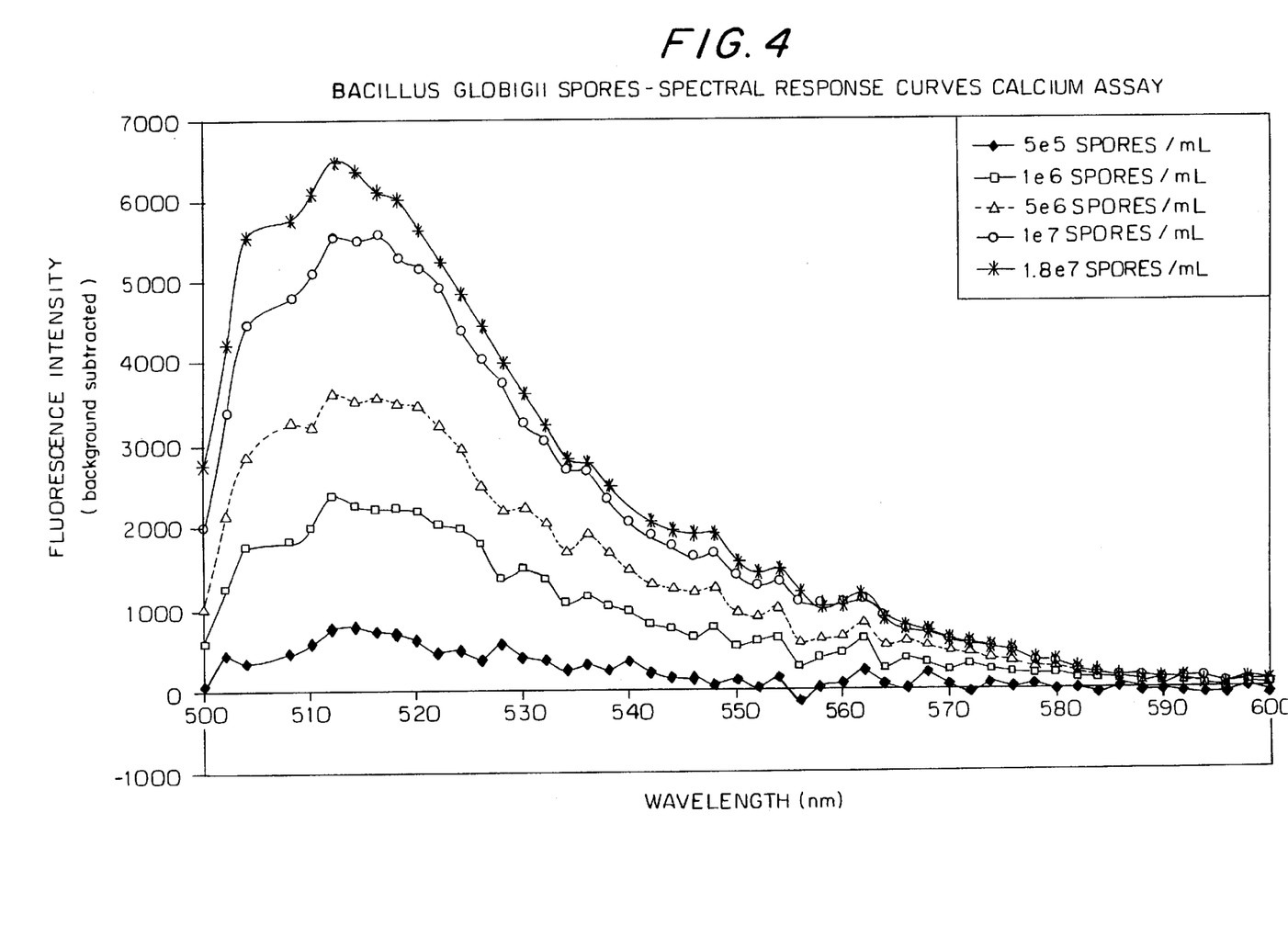
FIG. 4 shows spectral response curves of bacterial spores.

The spectral response curves resulting from spore/dye interaction are shown in FIG. 4. The data were collected using a 495LP emission filter, setting the excitation wavelength at 485 nm, and measuring the resulting fluorescence for 300 ms over a wavelength range of 500–600 nm. The peak fluorescence emission intensity occurs at 515 nm. Spectral data were analyzed by averaging the spectra of three replicates. A control measurement, no spores, was subtracted from all data points to eliminate background fluorescence. Although there is an immediate increase in fluorescence intensity when the spores are added to the sensing chemistry, the spores were allowed to incubate for 20 minutes. By incubating the spores for 20 minutes, the maximum fluorescence intensity increase is monitored without effects from evaporation of the micro droplet. The immediate change in fluorescence signal can be used as the basis for a real-time warning device.

Figure 5:
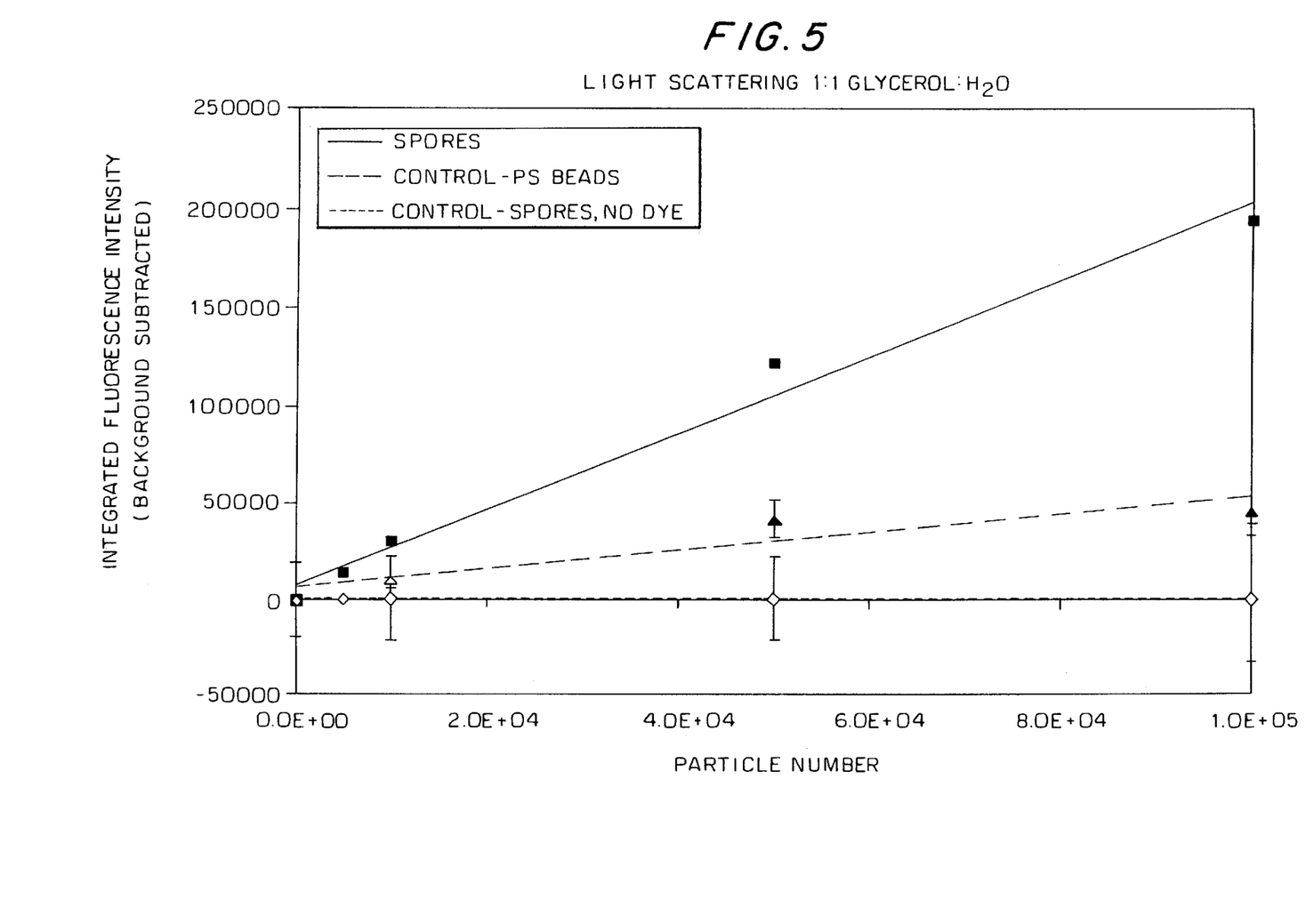
FIG. 5 shows light scattering in 1:1 glycerol:water.

The sensors of the present invention are intended for use in the field, and therefore the sensor response to potential interferents was characterized to avoid false positive or ambiguous results. One effect that may interfere with the sensor signal is light scattering off the dense spore coat. This effect was measured in two ways. First, the spore suspensions were replaced with 0.75 micron diameter polystyrene beads. The beads served as a mimic of the spore shape and size, i.e., ~1 micron in diameter. The resulting fluorescence intensity signal from the bead suspensions was negligible. Second, spore suspensions were introduced to the sensor without the indicator dye present. If light scattering by the spores were a factor, then the signal should be detectable even without the indicator dye present. In this case, the fluorescence signal intensity was virtually zero. These results indicated that light scattering by the spores is not a factor in this assay, as shown in FIG. 5.

Figure 6:
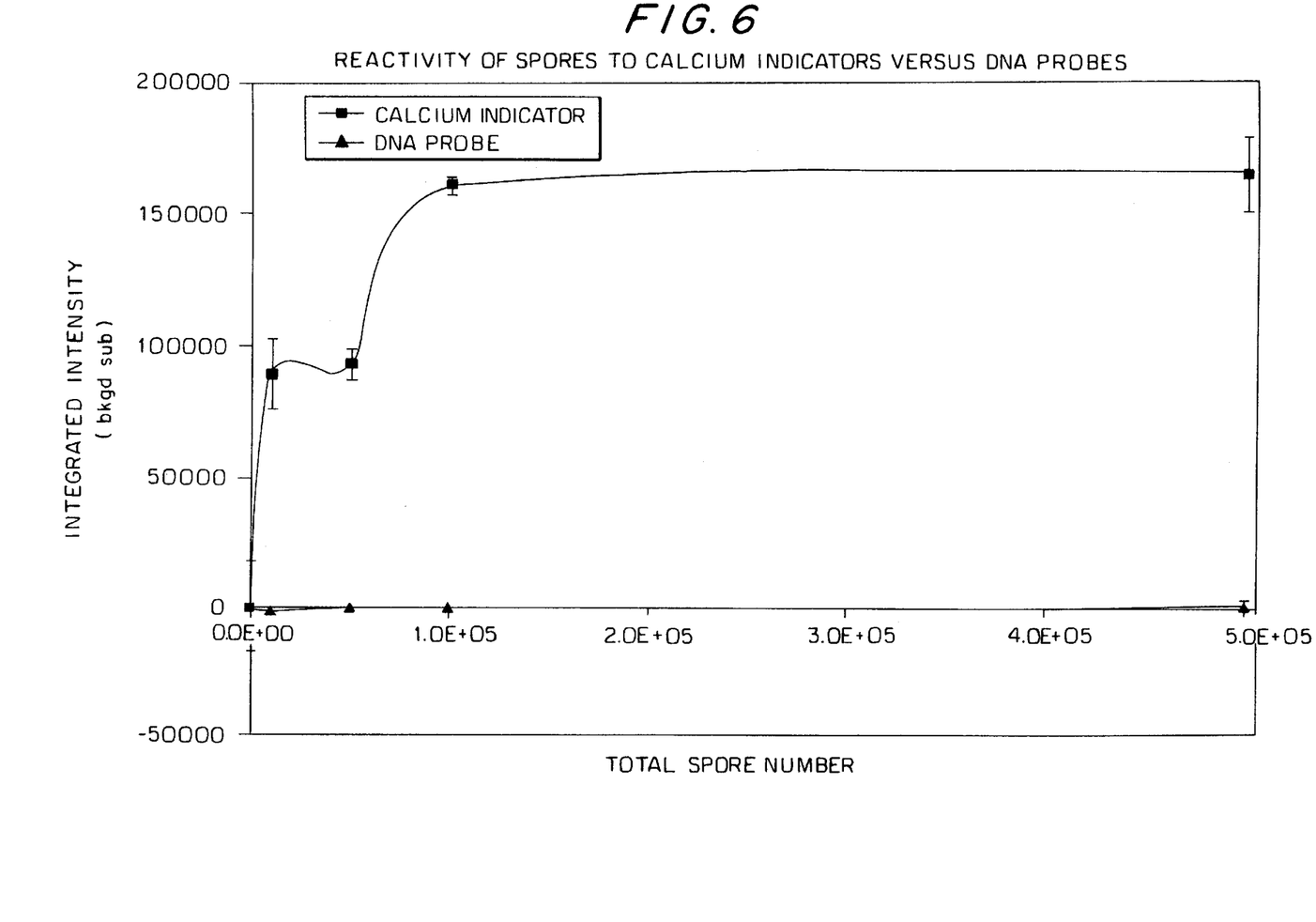
FIG. 6 shows reactivity of spores to calcium indicators vs. DNA probes.

FIG. 6 shows the reactivity of spores to calcium indicators versus DNA probes. The reactivity of the spores was characterized by exposing the spores to chemistries containing calcium indicators or DNA probes. The data were analyzed by averaging the integrated signal from three replicates and calculating the standard deviation. A control measurement was subtracted from all data points to eliminate background fluorescence. The fluorescence intensity resulting from the chemistry containing the DNA probe was virtually zero compared to the chemistry containing a calcium sensitive indicator. The data demonstrate the inability to stain spores using DNA probes.

Figure 7:
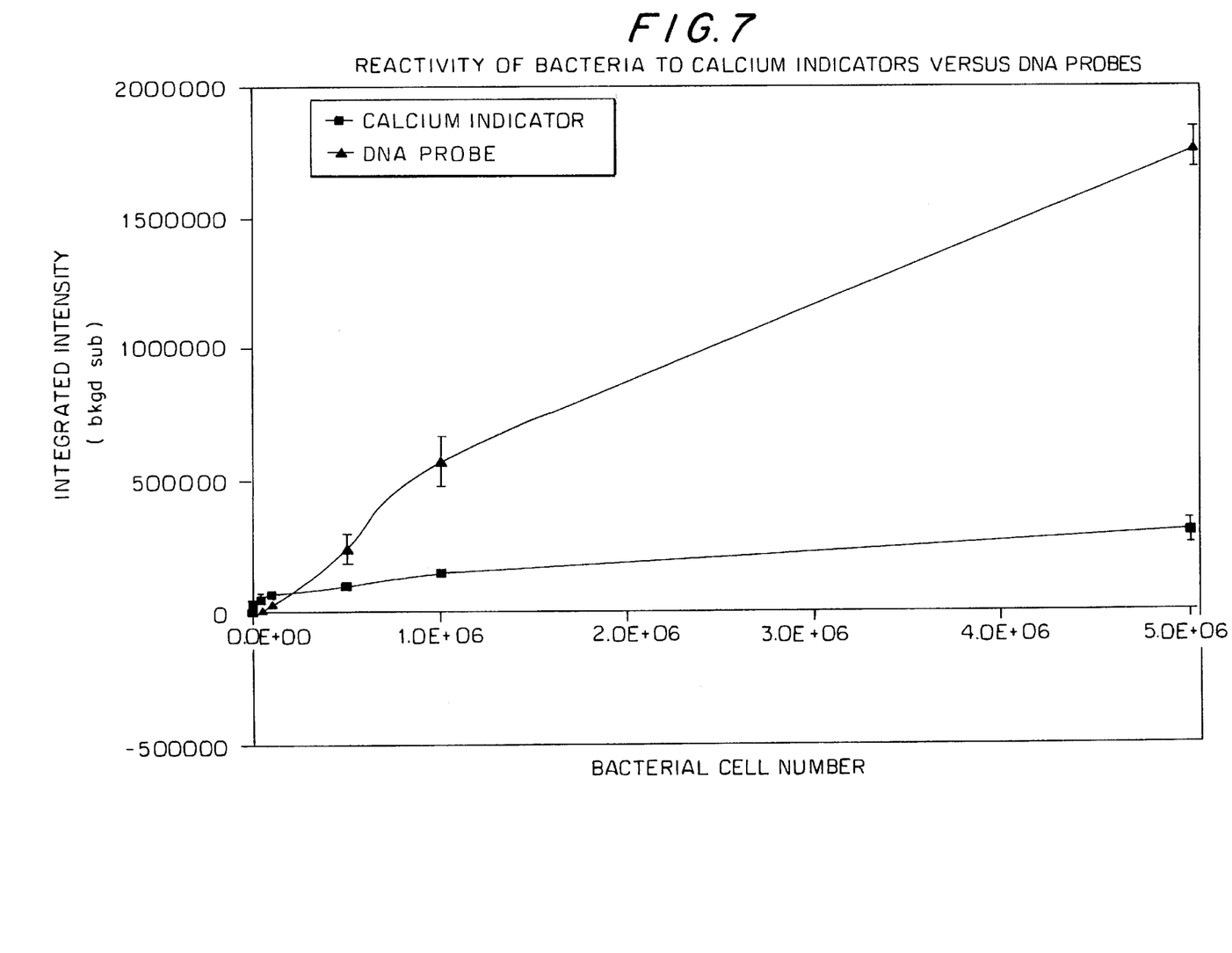
FIG. 7 shows reactivity of bacteria to calcium indicators versus DNA probes.

FIG. 7 illustrates the reactivity of bacteria to calcium indicators versus DNA probes. The reactivity of the bacteria was characterized by exposing the bacteria to chemistries containing calcium indicators or DNA probes. The data were analyzed by averaging the integrated signal from three replicates and calculating the standard deviation. A control measurement was subtracted from all data points to eliminate background fluorescence. The fluorescence intensity resulting from the chemistry containing the calcium-sensitive indicator was negligible compared to the chemistry containing a DNA probe. The data demonstrate the specificity of the calcium indicators for spores.

Figure 8:
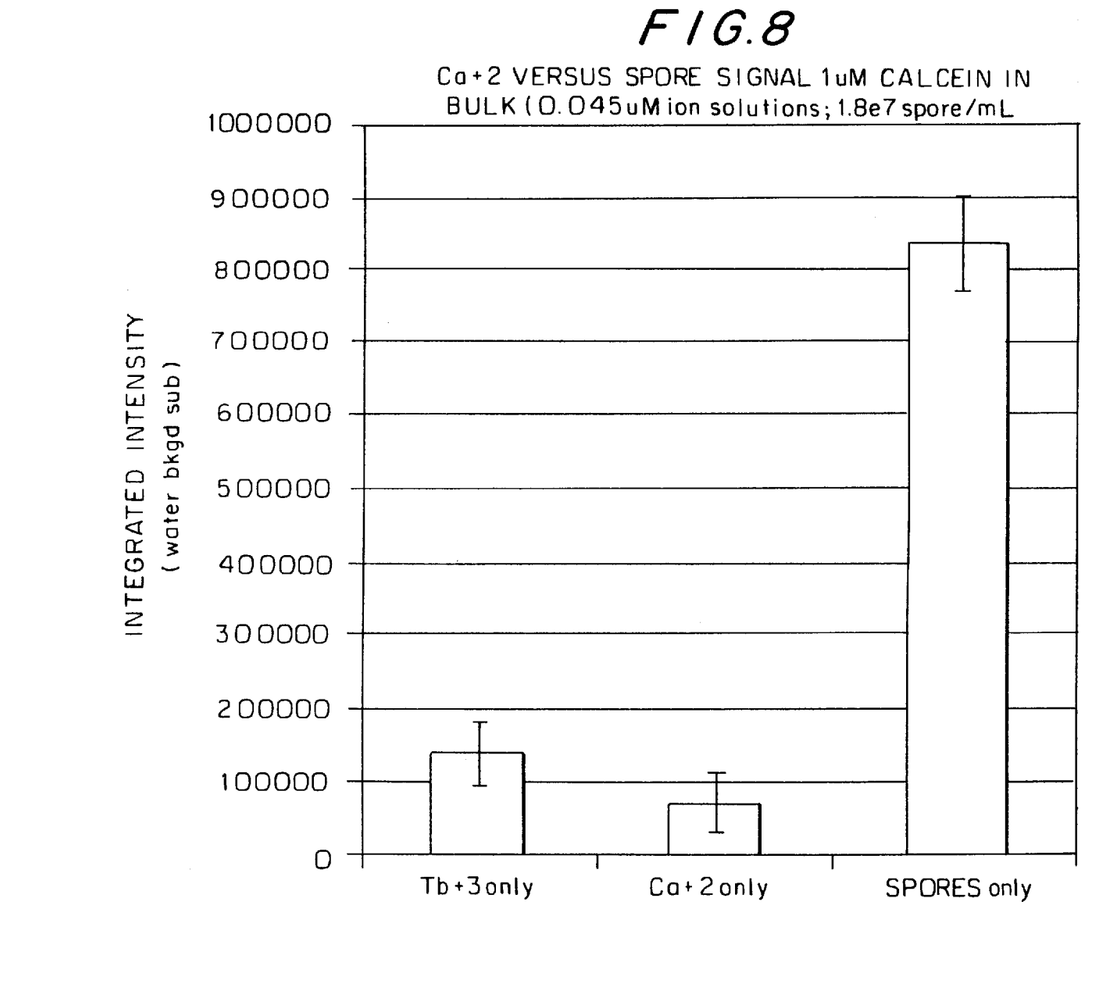
FIG. 8 shows signal enhancement in the presence of spores.

The fluorescence of free $Tb^{3+}$ and $Ca^{2+}$ were compared to the intensity from spore suspensions in bulk solution, as shown in FIG. 8. The data were analyzed by averaging the integrated signal from three replicates and calculating the standard deviation. A control measurement was subtracted from all data points to eliminate background fluorescence. The fluorescence increase from the free ions of $Tb^{3+}$ and $Ca^{2+}$ to spore suspensions is 510% and 1095%, respectively, as shown in FIG. 8.

Figure 9:
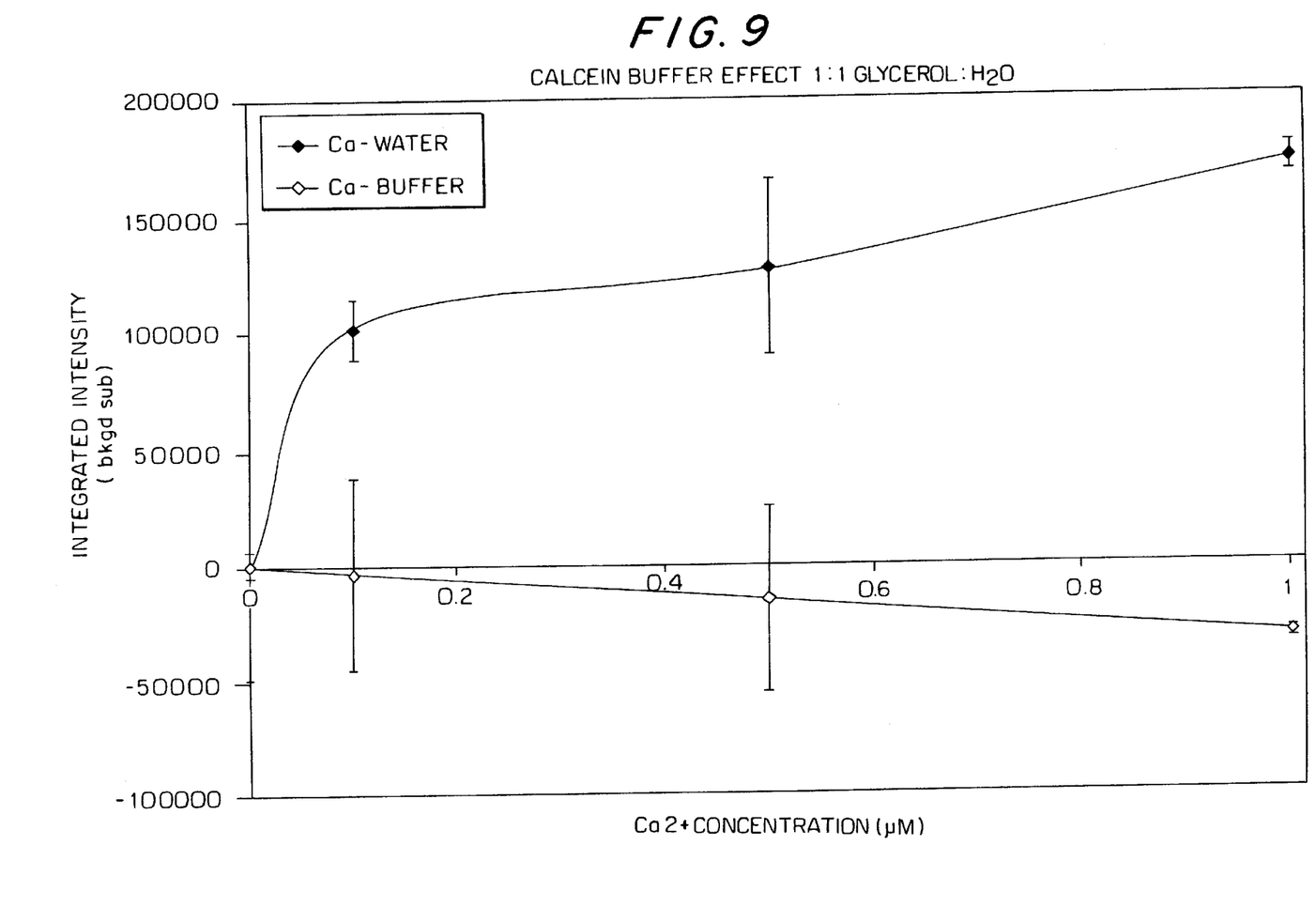
FIG. 9 shows the effect of calcein buffer in 1:1 glycerol:water.

The effect of buffer on the sensing chemistry was characterized by preparing a calibration curve of $Ca^{2+}$ in water versus $Ca^{2+}$ in Tris buffer. The data were analyzed by averaging the integrated signal from three replicates and calculating the standard deviation. A control measurement (no $Ca^{2+}$) was subtracted from all data points to eliminate background fluorescence. The fluorescence intensity response of $Ca^{2+}$ buffer to Calcein dye fell below the background measurement, as shown in FIG. 9, indicating that there is a significant buffer effect when compared to data taken in a water environment.

Figure 10:
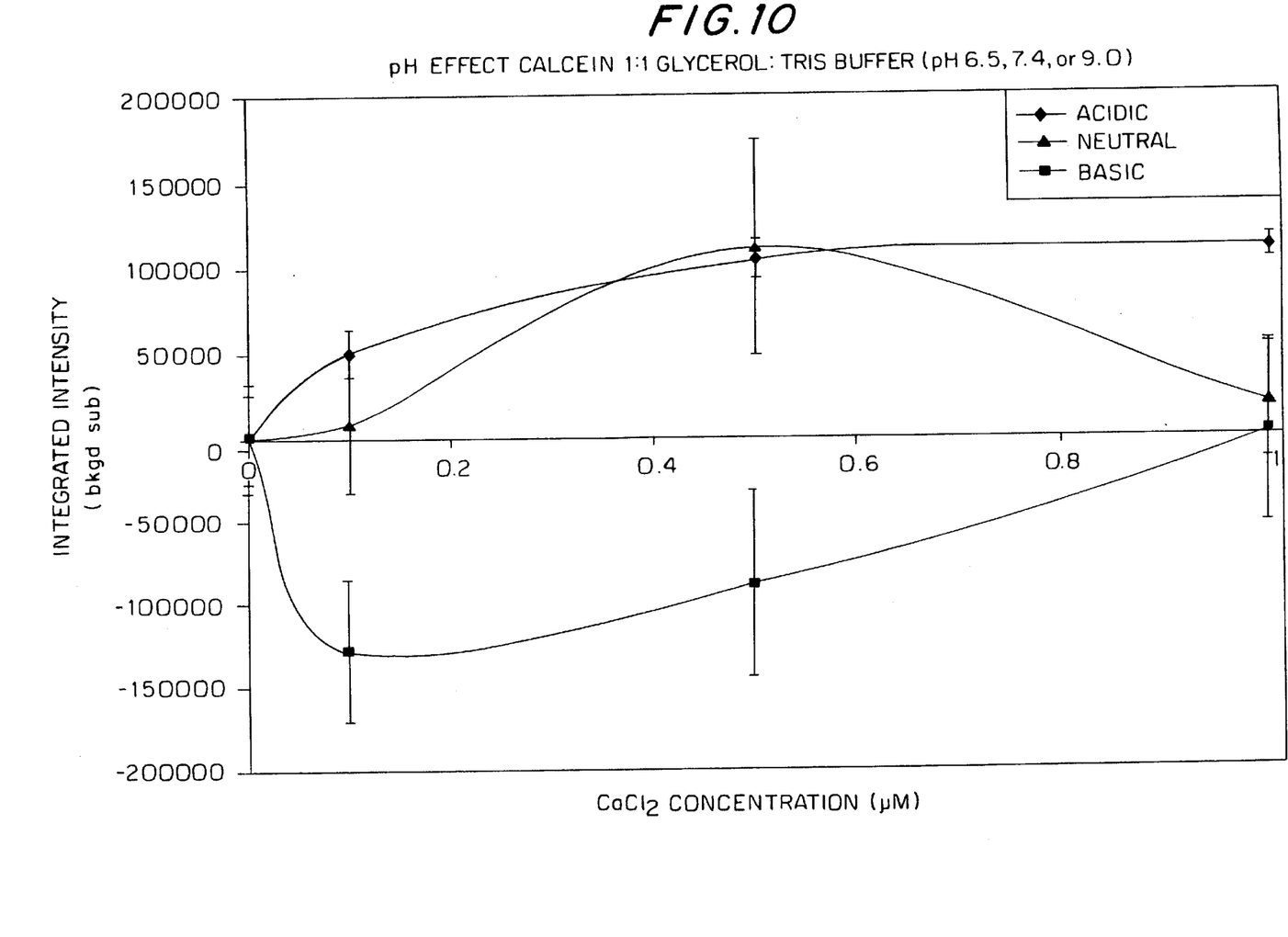
FIG. 10 shows the pH effect on calcein in 1:1 glycerol:Tris buffer.

The fluorescence signal from calcein in the presence of metal ions is pH dependant at very basic pH. Therefore, the effect of pH on the sensing chemistry was also tested. To test the pH effect, sensors were prepared by substituting Trizma (R) buffer at pH 6.5, 7.4, or 9.0 for the water. Calibration curves of $Ca^{2+}$ ion concentration at each pH were developed. The linearity of the curve was unaffected by the preparations at neutral and acidic pH. As shown in FIG. 10, elevated pH greatly altered the linearity of the curve. This correlates to previously published data detailing the pH dependence of Calcein dye at basic pHs (Wallach). Since the likelihood that spores will be present in a highly basic solution is low, the pH dependence at basic pHs should not be a factor in the practical implementation of sensing spores.

Table 2 shows the effects of potential interberents on the sensor. The data were compiled by averaging the background subtracted integrated intensity data from a minimum of three separate experiments (different chemistry preparations) to generate a representative fluorescence intensity value for *Pseudomonas aeruginosa* bacteria, MS2 bacteriophage (a viral BW simulant), Ragweed pollen, and *Penicillium roquefortil* mold spores. The normalized average integrated intensity of each material is relative to the spore values (100%). All of the biological interferents yield a normalized fluorescence intensity of 20% or less indicating that there is minimal interference in the sensor from other biological materials.

TABLE 2

| Biological Material Concentration | Concentration | Average Integrated Intensity | Normalized % |
|---|---|---|---|
| Bs Bacterial spores | 1.8 e7/mL | 228454 | 100 |
| Pa Bacterial spores | 1.8 e7/mL | 42248 | 18 |
| MS2 Virus | 1.8 e1/mL | 14184 | 6 |
| Pr Fungal spores | 1.3 e7/mL | −39588* | — |
| Ragweed pollen | 10,000/m$^3$ | 45370 | 20 |

*The fluorescence signal feel below background measurement, indicating that there is no sensitivity to fungal spores.

The sensor of the present invention combines a visibly excitable, fluorescent, calcium-sensitive indicator with optical fibers and disposable planar glass coupons to create a rapid, cost-effective and simple sensor. The advantages of the sensor of the present invention are threefold:

1. The ability to incorporate multiple sensors per coupon and directly measure the sample fluorescence without further washing or filtering steps dramatically decreases analysis time and reduces possible sources of error compared to conventional microbiological methods.

2. Using visibly excitable indicators effectively overcomes limitations introduced by laser and UV excitation sources required by other detection methods.

3. Cross-reactivity with other biological materials such as bacteria, pollen, viruses, and mold as well as interference from light scattering and pH, are negligible.

Many conventional detection technologies are hindered by time-consuming measurements, bulky equipment that is both costly and power consumptive, an d/or cross-reactivity with other biological materials. The speed, simplicity, and selectivity of the assay of the present invention, however, are advantageous for developing a hand-held or field portable bacterial spore detection and warning device.

Depending upon the user's particular requirements, any type of warning indicator can be used with sensors according to the present invention. Nonlimiting examples of such warning devices include audible and visible warning devices, such as bells, sirens, lights, and the like.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

REFERENCES (1) Perry, J. J,: Staley, J. T. *Microbiology: Dynamics and Diversity*, 2$^{nd}$ ed.; Harcourt Brace College Publishers: New York, 1997
(2) Madigan, M. T.; Martinko, J. M.; Parker, *J. Biology of Microorganisms*, 8$^{th}$ ed.; Prentice Hall: Upper Saddle River, N.J. 1997
(3) Tuminello, P. S.; Arakawa, E. T.; Khare, B. N.; Wrobel, J. M.; Querry, M. R.; Milham, M. E. *Applied Optics* 1997, 36, 2818–2824
(4) Beverly, M. B.; Basile, F.; Voorhees, K. J. *Rapid Communications in Mass Spectrometry* 1996, 10, 455–458
(5) Snyder, A. P.; Thornton, S. N.; Dworzanski, J. P.; Meuselaar, H. L. C. *Field Analytical Chemistry and Technology* 1996, 1, 49–59
(6) Bruno, J. G.; Kiel, J. L. *Biosensors & Bioelectronics* 1999, 14, 457–464
(7) Herman, L. M. F.; Vaerewijck, M. J. M.; Moermans, R. J. B.; Waes, G. M. A. V. J. *Applied and Environmental Microbiology* 1997, 63, 3139–3143
(8) Blake, M. R.; Weimer, B. C. *Applied and Environmental Microbiology* 1997, 63, 1643–1646
(9) Quinlan, J. J.; Foegeding, P. M. *Applied and Environmental Microbiology* 1997, 63, 482–487
(10) Scholl, P. F.; Leonardo, M. A.; Rule, A. M.; Carlson, M. A.; Antoine, M. D.; Buckley, T. J. *Johns Hopkins APL Technical Digest* 1999, 20, 343–351
(11) Pellegrino, P. M.; Fell, N. F.; Rosen, D. L.; Gillespie, J. B. *Analytical Chemistry* 1998, 70, 1755–1760
(12) Rosen, D. L.; Sharpless, C.; McGown, L. B. *Analytical Chemistry* 1997, 69, 1082–1085
(13) *ATCC Bacteria & Bacteriophages*, 19$^{th}$ ed. Pienta, P.; Tang, J.; Cote, R. eds 1996, 468–469
(14) Personal communication with Dr. Paul Pellegrino, U.S. Army Research Laboratory, 1999
(15) In subsequent experiments it was determined that the maximum response occurs in less than two minutes
(16) Wallach, D. F. H.; Steck, T. L. *Analytical Chemistry* 1963, 35, 1035–1044

What is claimed is:

1. A sensor for detecting bacterial spores comprising a fluorescent calcium-sensitive indicator;

a planar coupon in which the calcium-sensitive indicator is fixed, said planar coupon being affixed to the distal end of an optical fiber;
   whereby said optical fiber provides excitation light and collects fluorescence emission from the planar coupon.

2. The sensor according to claim 1, wherein the calcium-sensitive indicator is calcein.

3. The sensor according to claim 1, wherein more than one calcium indicator is fixed to the coupon.

4. The sensor according to claim 1, wherein the calcium sensitive indicator is incorporated in a viscous membrane.

5. The sensor according to claim 1 wherein the calcein is incorporated in glycerol.

6. A method for detecting bacterial spores comprising contacting a sensor comprising a planar coupon in which a fluorescent calcium-sensitive indicator is fixed with a sample, monitoring any change in fluorescence intensity of the sensor, and correlating the change in fluorescence intensity to the presence of bacterial spores.

7. The method according to claim 6 wherein the calcium-sensitive indicator is calcein.

8. The method for detecting bacterial spores comprising detecting the calcium concentration in bacterial spore coat using a fluorescent calcium indicator wherein the fluorescent calcium indicator is immobilized in a polymer membrane, and correlating the change in fluorescence intensity to the presence of bacterial spores.

9. The method according to claim 8 wherein the fluorescent calcium indicator is incorporated in glycerol.

* * * * *

UNITED STATES PATENT AND TRADEMARK OFFICE
CERTIFICATE OF CORRECTION

PATENT NO. : 6,498,041 B1
DATED : December 24, 2002
INVENTOR(S) : Mary Beth Tabacco and Laura C. Taylor It is certified that error appears in the above-identified patent and that said Letters Patent is hereby corrected as shown below:

<u>Column 1,</u>
Line 5, insert the following new section:
-- GOVERNMENT LICENSE RIGHTS
The U.S. Government has a paid-up license in this invention and the right in limited circumstances to require the patent owner to license others on reasonable terms as provided for by the terms of Contract No. DAAL01-908-C-0077 awarded by the U.S. Army. --

Signed and Sealed this

Twenty-sixth Day of April, 2005

JON W. DUDAS
*Director of the United States Patent and Trademark Office*